US007753835B2

(12) United States Patent
Van Der Lee et al.

(10) Patent No.: US 7,753,835 B2
(45) Date of Patent: Jul. 13, 2010

(54) RADIATION-SHIELDING CONTAINER ASSEMBLIES, RADIOACTIVE MATERIAL ADMINISTRATION DEVICES, AND METHODS OF USING THE SAME

(75) Inventors: Petrus Johannes Jozef Van Der Lee, Alkmaar (NL); Tim T. Horeman, Akersloot (NL)

(73) Assignee: Mallinckrodt Inc., Hazelwood, MO (US)

( * ) Notice: Subject to any disclaimer, the term of this patent is extended or adjusted under 35 U.S.C. 154(b) by 551 days.

(21) Appl. No.: 11/632,804

(22) PCT Filed: Sep. 2, 2005

(86) PCT No.: PCT/US2005/031411

§ 371 (c)(1),
(2), (4) Date: Jan. 16, 2007

(87) PCT Pub. No.: WO2006/135412

PCT Pub. Date: Dec. 21, 2006

(65) Prior Publication Data

US 2008/0086025 A1 Apr. 10, 2008

(30) Foreign Application Priority Data

Sep. 3, 2004 (EP) .................................. 04077471

(51) Int. Cl.
*A61N 5/00* (2006.01)

(52) U.S. Cl. .......................................................... 600/3

(58) Field of Classification Search ................. 600/1–8; 205/364; 206/365, 530, 540; 414/810; 250/506.1, 250/507.1, 515.1
See application file for complete search history.

(56) References Cited

U.S. PATENT DOCUMENTS

| | | | |
|---|---|---|---|
| 4,084,097 A | 4/1978 | Czaplinski et al. | |
| 4,144,461 A | 3/1979 | Glasser et al. | |
| 5,268,102 A | 12/1993 | Clay et al. | |
| 5,752,603 A * | 5/1998 | Faber | 206/530 |

(Continued)

FOREIGN PATENT DOCUMENTS

| | | |
|---|---|---|
| DE | 1240598 | 5/1967 |
| WO | WO 01/02048 | 1/2001 |
| WO | WO 2004/004787 | 1/2004 |

*Primary Examiner*—Charles A Marmor, II
*Assistant Examiner*—Christine D Hopkins

(57) ABSTRACT

The present invention, in some embodiments, relates to radiation-shielding containers for housing radioactive materials. For example, some container assemblies of the invention include a body and a lid both including radiopaque material, and together defining a receiving space for radioactive material. Each of the body and lid has a closure surface that is in close proximity with the closure surface of the other when the container assembly is in a closed condition. The closure surfaces of these container assemblies may be configured such that they run substantially entirely at an angle to a local direction of radiation emanating from the radioactive material. In other words, these closure surfaces may be oriented such that they are misaligned with radiation emanating from within the container assembly. The present invention, in some embodiments, relates to devices for administration of radioactive material (e.g., radiopharmaceutical capsule) to patients.

24 Claims, 10 Drawing Sheets

U.S. PATENT DOCUMENTS

| | | | | |
|---|---|---|---|---|
| 5,834,788 | A | 11/1998 | Fu et al. | |
| 5,944,190 | A | 8/1999 | Edelen | |
| 6,106,455 | A | 8/2000 | Kan | |
| 6,450,936 | B1 | 9/2002 | Smith, III et al. | |
| 2002/0178566 | A1 * | 12/2002 | Reich | 29/426.5 |
| 2004/0135105 | A1 | 7/2004 | Hutcheson | |

* cited by examiner

RADIATION-SHIELDING CONTAINER ASSEMBLIES, RADIOACTIVE MATERIAL ADMINISTRATION DEVICES, AND METHODS OF USING THE SAME

FIELD OF THE INVENTION

The invention relates to radiation-shielding containers for radioactive materials, such as containers used for transporting and handling radioactive materials (e.g., iodine $I^{131}$) that are used in medical diagnostic and/or therapeutic procedures.

BACKGROUND

A conventional container for radioactive materials typically includes a radiation-shielding body in which the radioactive material is received, and a radiation-shielding lid to be placed on the body to enclose the radioactive material in the container. Both the body and lid tend to be made of lead or lead alloy. In order to prevent radiation emanating from the radioactive material from leaking out of the container between the body and the lid, one of these parts usually includes an annular groove or recess having a substantially rectangular cross-section, while the other part includes a mating annular ridge. This particular design may be characterized as a complimentary stepped configuration of the respective contacting surfaces.

The stepped configuration of the interface between body and lid of the container generally includes one or more pairs of concentric and parallel contacting surfaces. For instance, a first pair of contacting surfaces may be formed by the edge of the body and the lid, and a second by the annular ridge and the groove. Due to manufacturing tolerances, the body and lid of the container may abut along only one of these pairs of contacting surfaces. This means that an undesired gap may be defined between the contacting surfaces of the other pair. Some may find the presence of such a gap disadvantageous, because, for example, the design of the contacting surfaces may not prevent radiation from entering into the gap, thus potentially reducing the container's ability to effectively prevent escape of radiation in some cases. Some may find the presence of such a gap disadvantageous, because, for example, an effective wall thickness of the container at that point may be reduced enough, in some cases, to enable radiation to get through the container at that point. As another possible detriment, some may find that various conventional containers fail to prevent radioactive material from moving about in the container to a location where radiation may be aligned with and/or concentrated near the gap between the contacting surfaces.

SUMMARY

A first aspect of the present invention is directed to a radiation-shielding container assembly. This container assembly includes a radiation-shielding body and a radiation-shielding lid, both of which include substantially radiopaque material (e.g., lead, tungsten, depleted uranium, and/or the like). The body of the container assembly has a receiving space at least partially defined therein. This receiving space is generally designed to accommodate a radioactive material (e.g., capsular dose of iodine $I^{131}$ for a medical patient). When this container assembly is in a closed condition, a closure surface of the body faces and is in close proximity to (e.g., in contact with or very near contact with) a closure surface of the lid. Further, at least an inner most portion of the closure surface of the body (i.e., portion nearest the receiving space) is oriented such that radiation emanating directly from the radioactive material is substantially prevented from travelling along the inner most portion of the closure surface of the body. For instance, an inner most portion of the closure surface of the body and an inner most portion of the closure surface of the lid may be oriented such that radiation emanating directly from the radioactive material is not directed between those portions of the closure surfaces in a direction substantially parallel to those portions. Incidentally, radiation that has emanated from radioactive material and that has not been deflected may be said to be directly emanated. By comparison, radiation that has emanated from radioactive material and that has been deflected (e.g., off of a radiation deflecting object) may be said to be directly emanated prior to the initial deflection and indirectly emanated after the initial deflection.

The container assembly of this first aspect may include an imaginary centre line that longitudinally extends through both the body and the lid. In some embodiments, the inner most portion of the body's closure surface may be substantially perpendicular to or acutely oriented relative to the centre line. In some embodiments, a substantial entirety (e.g., greater than about 95%) of the closure surface of the body is non-parallel (e.g., perpendicular, acutely oriented, and/or obtusely oriented) to the centre line. Incidentally, the body and lid of the container assembly may exhibit any of a number of appropriate designs. For instance, in some embodiments, the body and lid are substantially rotationally symmetrical about the centre line. In other embodiments, one or both the body and the lid may not be substantially rotationally symmetrical about the centre line.

Still referring to the first aspect of the present invention, the inner most portion of the body's closure surface may, at least in some embodiments, be substantially frustoconical. In some embodiments, a substantial majority (e.g., no less than about 50%) of the body's closure surface of the body may be oriented such that radiation directly emanating from the radioactive material is substantially prevented from travelling there along. Some embodiments may have a substantial entirety (e.g., no less than about 95%) of the closure surface of the body being oriented such that radiation directly emanating from the radioactive material is substantially prevented from travelling there along. Incidentally, radiation that "travels along" a particular portion of closure surface refers to radiation that radiates in a direction substantially aligned with and very near the particular portion of the closure surface (e.g., through a gap between the closure surfaces of the lid and the body when the container assembly is in a closed condition).

The body and lid may be configured and dimensioned such that radioactive material located in the receiving space of the container assembly may be surrounded by a substantially constant amount of radiopaque material in all directions. This feature of the container assembly may be characterized by some as beneficially providing at least generally uniform radiation shielding. Accordingly, in some embodiments, the shape and/or dimensions of the body and/or lid of the container assembly may be at least somewhat dependent upon the shape and/or dimensions of the radioactive material to be disposed in the receiving space. For instance, in some embodiments of the container assembly, peripheral edges of one or both the body and the lid may be chamfered, rounded, or the like.

Some embodiments of the first aspect of the invention may include a vial that is disposable in the receiving space of the container assembly. For instance, the vial may include a base that is disposable into and releasably attachable to the body.

Likewise, the vial may include a cap that is releasably attachable to the lid. For instance, the base may be snap-fitted to the body, and/or the cap may be snap-fitted to the lid. Other embodiments may exhibit other appropriate manners of releasably attaching one or both the body and lid to the corresponding base and cap. In some embodiments, the cap of the vial may include a plug-like part that protrudes into the base of the vial when the container assembly is in a closed condition. The body and/or lid of the container assembly may include an insert disposed in a receptacle thereof. One or more of the inserts may include an opening therethrough. In some embodiments, a projection of the base can be snap-fitted into the insert of the body, and/or a projection of the cap can be snap-fitted into the insert of the lid. While the vial may be made out of any appropriate material (e.g., plastic), in some embodiments, it is made of a material that is at least one of radiotransparent (i.e., transparent to radiation) and radiotranslucent (i.e., allows radiation to pass through in an at least generally diffuse or reduced fashion).

Still referring to the first aspect of the invention, the container assembly may include a case that includes a receptacle and a cap. The receptacle of the case is generally designed to accommodate at least a portion of the body. The cap of the case is releasably connectable to the receptacle of the case and is generally designed to accommodate at least a portion of the lid. In some embodiments, the cap may be dimensioned such that an internal, hollow space is defined between a top surface of the lid and the cap. As with the vial, the case may be made of any appropriate material such as, for example, a radiotransparent and/or radiotranslucent material.

A second aspect of the invention is direct to a method of inhibiting escape of radiation from a radiation-shielding container assembly. This container assembly has a body and a lid, both of which include radiopaque material. The body has a recess defined therein to accommodate radioactive material. Further, a closure surface of the body faces and is in close proximity to a closure surface of the lid when the container assembly is in a closed condition. With regard to the method, radioactive material is disposed in the recess of the body. The radioactive material is disposed in the recess such that radiation directly emanating from the radioactive material is at least substantially prevented (e.g., precluded) from travelling between the closure surface of the lid and the closure surface of the body. In some embodiments, an entirety of the radioactive material is disposed within the recess so that no portion of the material extends through an imaginary reference plane including a portion of the closure surface of the body that is closest to a bottom of the body. In some embodiments, the radioactive material may be enclosed in a vial that is at least one of radiotransparent and radiotranslucent. At least a portion of this vial may be disposed in the recess of the body.

Yet a third aspect of the invention is directed to a radiopharmaceutical administration assembly that includes a first receptacle (e.g., a vial) having a radiopharmaceutical disposed therein, and a substantially tubular administration device releasably connectable (e.g., via a first end thereof) to the first receptacle and sized to allow the radiopharmaceutical to pass therethrough. The administration device may be designed to be releasably connected to the first receptacle in any of a number of appropriate manners. For instance, the administration device may be designed to be snap-fitted to the first receptacle. As an example, the first end of the administration device may include a plurality of fingers that are arranged for engaging a peripheral edge of the first receptacle.

Still referring to the third aspect of the invention, the administration device of some embodiments may be said to exhibit first and second diameters. The first diameter is generally located toward the first end of the administration device, and the second diameter is generally located toward an opposing second end of the administration device. The first diameter may be smaller than the second diameter.

Some embodiments of the third aspect may include a second receptacle designed to accommodate at least a portion of the first receptacle. This second receptacle may be made from a number of appropriate materials. For instance, the second receptacle of some embodiments is made of radiopaque material.

Still yet a fourth aspect of the invention is directed to a method of using a radiation-shielding container assembly that has a body and a lid, both of which include radiopaque material. The body of the container assembly generally has a recess defined therein to accommodate a radiopharmaceutical therein. With regard to the method of this fourth aspect, a substantially tubular administration device is connected (e.g., releasably connected) to a vial that is at least partially disposed in the recess of the body while the radiopharmaceutical is at least partially disposed in the vial. This connection may be accomplished in any appropriate manner, such as, for example, by snap-fitting the administration device to the vial. Next, the radiopharmaceutical is caused to leave the vial and travel through the administration device. For example, the administration device having the vial connected thereto may be tipped so that gravity causes the radiopharmaceutical to leave the vial and move through the administration device (e.g., toward a mouth of a patient). The vial may be removed from the recess of the body while the administration device is connected to the vial. This removal of the vial from the recess may be accomplished before or after the radiopharmaceutical is caused to leave the vial. The removal of the vial from the recess may be accomplished by lifting the administration device away from the body (e.g., the recess thereof) of the container assembly. In some embodiments, the remove of the vial from the recess may include relieving a snap connection that connects the vial and the body. While this fourth aspect of the invention has been briefly described in regard to radiopharmaceuticals, it should be noted that the administration device of this fourth aspect may have application in relation to non-radioactive pharmaceuticals as well.

Various refinements exist of the features noted in relation to the above-mentioned aspects of the present invention. Further features may be incorporated in the above-mentioned aspects of the present invention as well. These refinements and additional features may exist individually or in any combination. For instance, various features discussed below in relation to any of the illustrated embodiments of the present invention may be incorporated into any of the above-described aspects of the present invention, alone or in any combination.

BRIEF DESCRIPTION OF THE FIGURES

The invention will now be illustrated by way of various exemplary embodiments, with reference being made to the annexed figures, in which.

DETAILED DESCRIPTION OF THE ILLUSTRATED EMBODIMENTS

Figure 2:
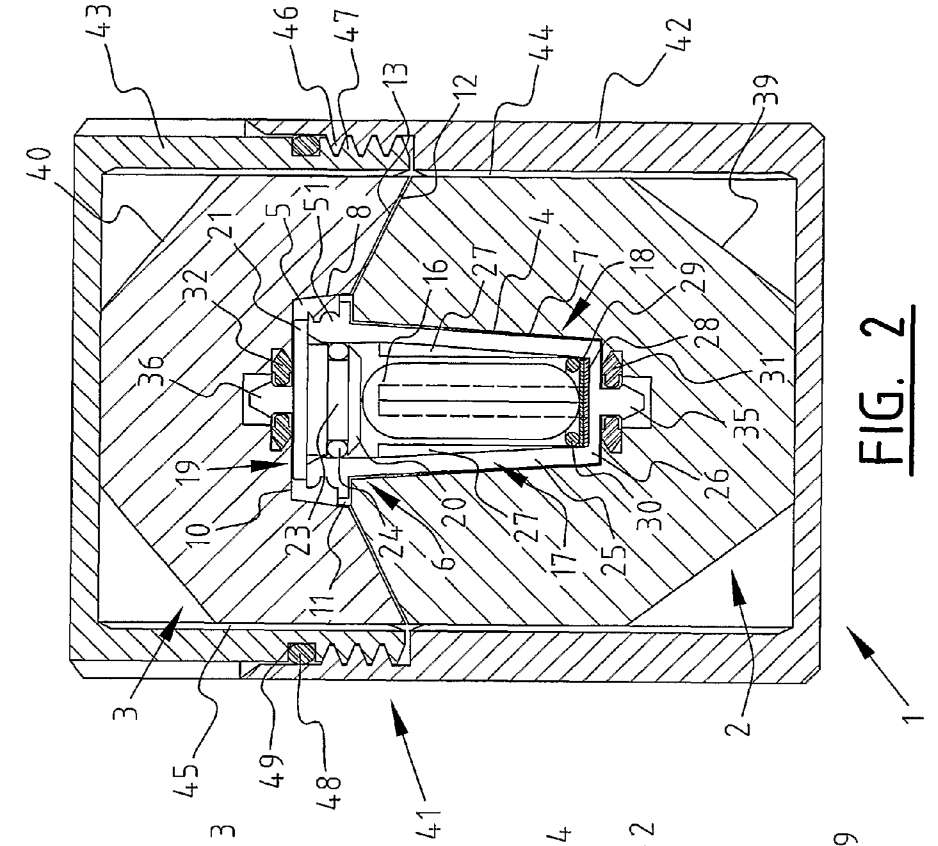
FIG. 2 is a cross-section of the container of FIG. 1 in a closed condition located in a receptacle and having a capsule of radioactive material disposed therein.

FIG. 2 shows a radiation-shielding container 1 that may be utilized to enclose radioactive material (e.g., for safe transporting and/or handling of the radioactive material). This container 1 includes a body 2 and a lid 3, each of which is made of radiopaque material (e.g. lead, tungsten, depleted uranium, and/or the like). While they may exhibit any of a number of appropriate designs and shapes, both the body 2 and the lid 3 are substantially rotationally symmetrical about an imaginary centre line $C_L$ (i.e., central reference axis) of the container 1 (FIG. 1) with the body 2 being substantially cylindrical and the lid 3 being substantially disc-shaped. The body 2 has a recess 4 defined therein that is bounded by a substantially cylindrical wall 14. The lid 3 has a recess 5 defined therein as well; however, the recess 4 in the body 2 tends to be deeper than the recess 5 in the lid 3. It should be noted that in other embodiments, the depth of the recesses 4, 5 may be substantially similar, while in still other embodiments, the recess 5 may be deeper than the recess 4. These recesses 4, 5 may be said to collectively define a receiving space 6 of the container 1 for accommodating radioactive material. For reasons to be discussed later, one or both of the recesses 4, 5 may have tapered side walls 7, 8 (respectively) and/or doubly stepped bottoms 9, 10 (respectively). The body 2 of the container 1 may include one or more lugs 11 that protrude from a peripheral edge 15 of the recess 4. For instance, the container 1 is shown as including two lugs 11 disposed on opposite sides of the centre line $C_L$. As will be discussed in more detail below, these lugs 11 are utilized to prevent rotational movement of a vial disposed in the recess 4 of the body 2 (relative to the body 2). It should be noted that other embodiments of the body 2 may not include the lugs 11. Some embodiments of the body 2 may include other appropriate mechanisms to substantially prevent rotational movement of a vial disposed therein (relative to the body).

The body 2 and lid 3 of the container 1 may be joined so that respective closure surfaces 12, 13 thereof are in very close proximity with one another and are preferably in contact. These closure surfaces 12, 13 are shown as being annularly disposed about the receiving space 6 of the container 1. Moreover, these closure surfaces 12, 13 are configured such that at least a portion of each of the closure surfaces (e.g., an innermost portion closest to the centre line $C_L$) is misaligned with radiation that is being emitted by the radioactive material in the container 1. In some embodiments, a majority of each of the closure surfaces is misaligned with radiation that is being emitted by the radioactive material in the container 1. In other embodiments, a substantial entirety of each of the closure surfaces is misaligned with radiation that is being emitted by the radioactive material in the container 1. In the illustrated embodiment, this misalignment is achieved by designing the closure surface 12 associated with the cylinder wall 14 of the body 2 to exhibit a substantially frustoconical configuration, and by designing the closure surface 13 surrounding the recess 5 in the lid 3 to exhibit what may be characterized as a substantially complimentary downward slope. As one characterization of the closure surface 12, it may be said that this closure surface 12, two-dimensionally speaking, includes a substantially linear portion that extends radially outwardly (i.e., away from the centre line $C_L$). As this substantially linear portion of the closure surface 12 extends radially outwardly, this substantially linear portion also tends to exhibit a downward slope (e.g., at least generally toward a bottom surface 37 of the body 2). Again, two-dimensionally speaking, this substantially liner portion of the closure surface 12 may refer to a substantial majority of the closure surface 12, or even a substantial entirety of the closure surface 12 (as shown in FIG. 1).

Figure 1:
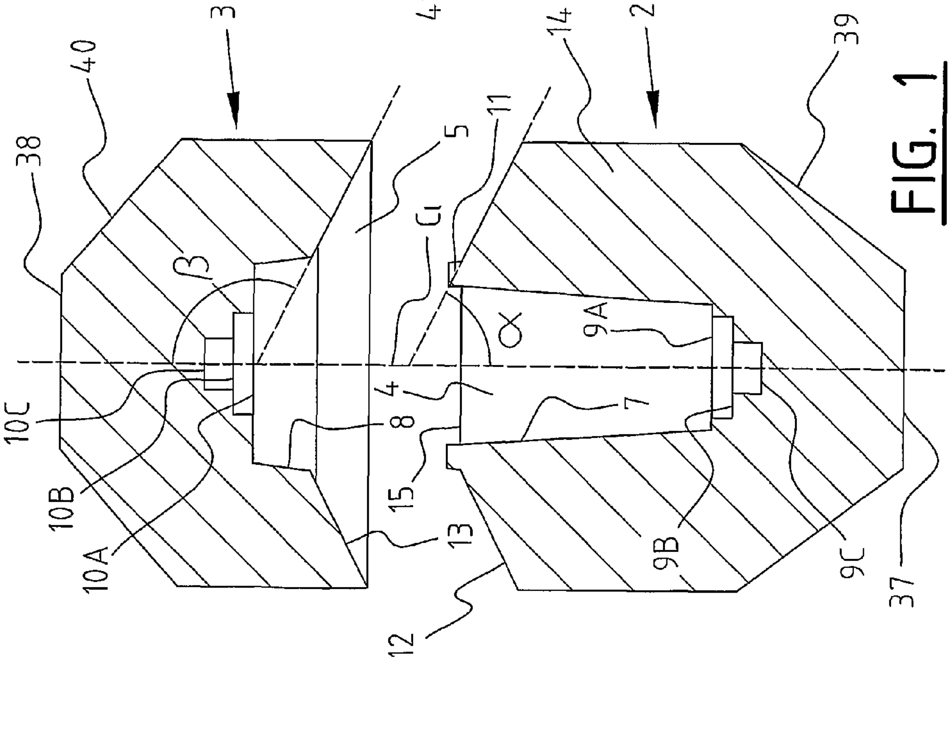
FIG. 1 is a cross-section of one embodiment of a body and lid of a radiation-shielding container of the invention.

Still referring to FIG. 1 and in some other embodiments, it may be said that one of the body 2 and the lid 3 has a closure surface (or at least a substantially linear portion thereof as described above) that is radially oriented at an angle α relative to the centre line $C_L$ that is acute (i.e., angle greater than 0 degrees and less than 90 degrees), and another of the body 2 and the lid 3 has a closure surface that is radially oriented at an angle β relative to the centre line $C_L$ that is obtuse (angle greater than 90 degrees and less than 180 degrees). In some embodiments, one of the closure surfaces (or at least a substantially linear portion thereof) is radially oriented at an angle α between about 30 degrees and about 90 degrees relative to the centre line $C_L$, while the other closure surface (or at least a substantially linear portion thereof) is radially oriented at an angle β of between about 90 degrees and about 150 degrees relative to the centre line $C_L$. In some embodiments, one of the closure surfaces (or at least a substantially linear portion thereof) is radially oriented at an angle α between about 40 degrees and about 90 degrees relative to the centre line $C_L$, while the other closure surface (or at least a substantially linear portion thereof) is radially oriented at an angle β of between about 90 degrees and about 140 degrees relative to the centre line $C_L$. In some embodiments, one of the closure surfaces (or at least a substantially linear portion thereof) is radially oriented at an angle α between about 50 degrees and about 90 degrees relative to the centre line $C_L$, while the other closure surface (or at least a substantially linear portion thereof) is radially oriented at an angle β of between about 90 degrees and about 130 degrees relative to the centre line $C_L$. While not always the case, it is generally preferred that the sum of the two angles α, β associated with the closure surfaces (or at least the substantially linear portions thereof) relative to the centre line $C_L$ is equal to about 180 degrees. Incidentally, it should be noted that these angles α, β are measured in a manner so that a portion of the corresponding body 2 or lid 3 is included inside the angle.

Since a significant portion of the receiving space 6 is defined by the recess 4 in the body 2 of the container 1, this is where the radioactive material tends to be placed. As shown in FIG. 2, an entirety of the radioactive material (here, an orally administrable radiopharmaceutical capsule 16) may be positioned in the recess 4 of the body 2 of the container 1 so that no portion of the radioactive material extends beyond an opening into the recess 4. In other embodiments, an entirety of the capsule 16 may be positioned in the recess 4 of the body 2 so that no portion of the radioactive material extends through an imaginary place that includes a portion of the closure surface 12 that is nearest a bottom of the body 2. Because of both the location of the radioactive material in the container 1 and the orientation of the closure surfaces 12, 13 relative to the radiation being emitted from the radioactive material, the radiation is misaligned with the closure surfaces 12, 13. As such, even if a small gap exists between the closure surfaces 12, 13 (e.g., because of a manufacturing tolerance and/or damage) when the container 1 is closed, the design of the container 1 combined with the positioning of the radioactive material therein tends to prevent radiation leakage from the container 1. In this respect, it should be noted that the gap illustrated between the closure surfaces 12, 13 shown in FIG. 2 may not (and preferably does not) actually exist.

In order to promote a positioning of the radioactive material such that radiation is substantially prevented from being in line with the closure surfaces 12, 13, the container 1 may include an appropriate positioning mechanism for the radioactive material. In the illustrated embodiment, which is particularly suited for use with radioactive material packed in single dose capsule 16, the positioning mechanism refers to a vial 17 that may be fixed in the receiving space 6 of the container 1. Internal dimensions of this vial 17 may at least generally correspond with outer dimensions of the capsule 16 to hinder movement of the capsule 16 relative to and when disposed in the vial 17. It should be noted that some embodiments include vials that exhibit any of a number of alternate container/packaging designs. Incidentally, the term "capsule" herein generally includes within the scope of its definition, orally administrable capsules, pills, tablets, pellets, caplets, and the like.

Figure 4:
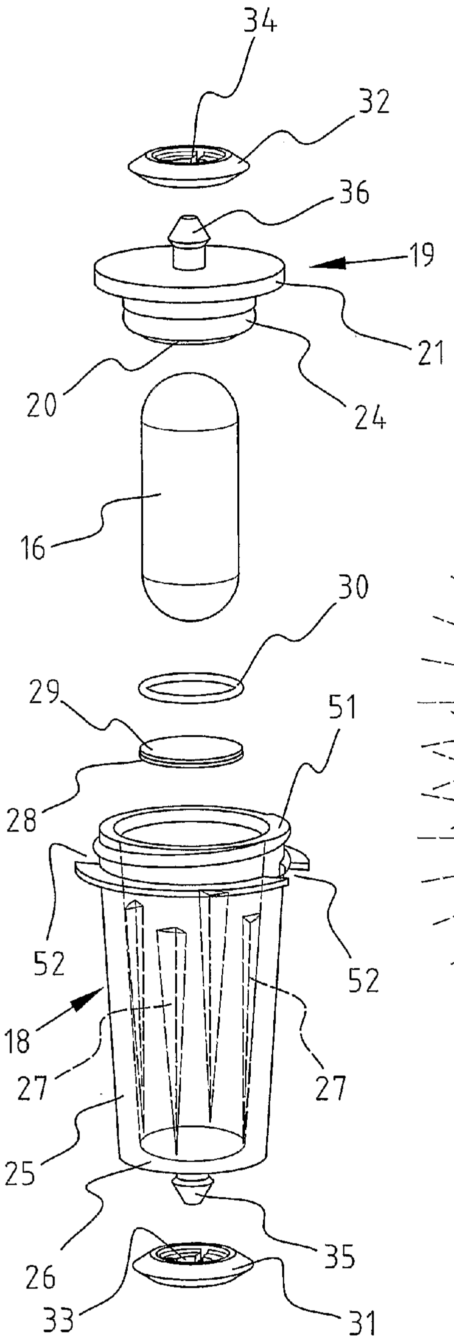
FIG. 4 is an exploded perspective view of a vial used in the container of FIGS. 1 to 3.

Referring to FIG. 4, the vial 17, which may be manufactured from any appropriate material (e.g., a gas-tight synthetic material such as PETP), includes a base 18 and a cap 19 attachable to the base 18. The cap 19 has a plug-like part 20 that extends into an opening of the base 18 when the cap 19 and base 18 are connected with one another. In addition, the cap 19 includes a flange 21 designed to abut a peripheral edge 51 of the base 18 when the cap 19 and base 18 are connected with one another. A groove 23 may be defined in the plug-like part 20 of the cap 19. This groove 23 may be designed to accommodate an O-ring 24 made of a resiliently flexible material (e.g., rubber or another elastomer) to promote a sealing the vial 17 when the base 18 and cap 19 are connected with one another.

While not always the case, the base 18 of the vial 17 is shown as having at least portions that substantially conform to the recess 4 in the body 2 to inhibit undesired movement of the vial 17 relative to the body 2 of the container 1. In this particular embodiment, the base 18 includes a tapering sidewall 25 and a substantially flat bottom 26. In addition, angularly spaced ribs 27 protrude from the sidewall 25 into an interior opening of the base 18 to provide lateral support for the capsule 16. One or more filters may be disposed within the interior of the base 18. For instance, arranged on the bottom 26 of the base 18 may be an active carbon filter layer 28, a hydrophobic filter layer 29 and a locking ring 30 for substantially immobilizing the filter layers 28, 29 relative to the bottom 26 of the base 18. In should be noted that other embodiments may include additional or alternative filtering features and/or locking features. In a closed condition of the vial 17 (i.e., when the base 18 and cap 19 are attached to one another), the distance between the plug-like part 20 of the cap 19 and the filter layers 28, 29 in the base 18 preferably substantially corresponds with the length of the capsule 16, thus inhibiting undesired movement of the capsule 16 in the receiving space 6. A diameter of the capsule 16 may be smaller (e.g., slightly smaller) than or substantially equal to the distance between opposing ribs 27, so that the capsule 16 may be substantially immobilized yet easily withdrawn from the vial 17.

Figure 3:
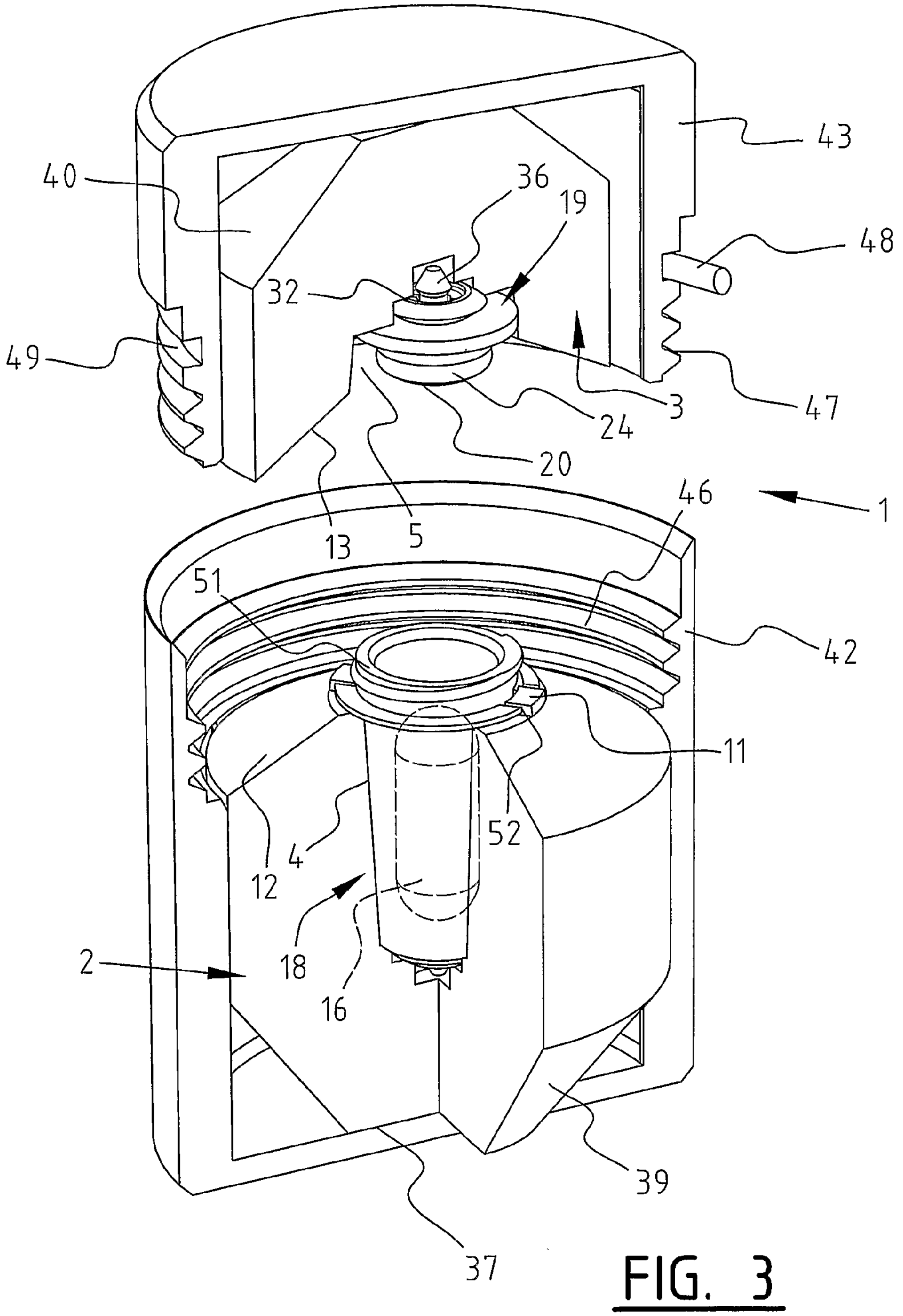
FIG. 3 is a perspective view of the body and lid of the container and receptacle of FIG. 2, with parts broken away for clarity.

Referring to FIGS. 2-3, the base 18 and cap 19 may be releasably fixed in the body 2 and lid 3 (respectively) of the container 1. While this releasable fixation may be achieved in any of a number of manners, it is achieved by snap-fitting in the illustrated embodiment. Each of the base 18 and the cap 19 may include a protrusion 35, 36 (respectively) shaped as pins having expanded heads. The protrusion 35 tends to be associated with (e.g., attached to or extending out from) a bottom surface 37 of the base 18, and the protrusion 36 tends to be associated with a top surface of the cap 19. Since lead tends to be a relatively soft and non-flexible material, inserts 31, 32 of a harder and more flexible material (e.g., a plastic) may be butted into first stepped portions 9B, 10B of bottoms 9, 10 of the recesses 4, 5 (respectively). These inserts 31, 32 may include openings 33, 34 (respectively) into which the protrusions 35, 36 of the base 18 and cap 19 (respectively) may be snapped. The protrusions 35, 36 may be received in the space defined by second stepped portions 9C, 10C of the recess bottoms 9, 10 (respectively). It should be noted that some embodiments may not include one or more of the inserts 31, 32. For instance, the material utilized to make up the body 2 and/or the lid 3 of some embodiments may be sufficient to withstand the protrusions 35, 36 being snap-fitted directly into openings integrally defined in the body 2 and/or lid 3.

Figure 5:
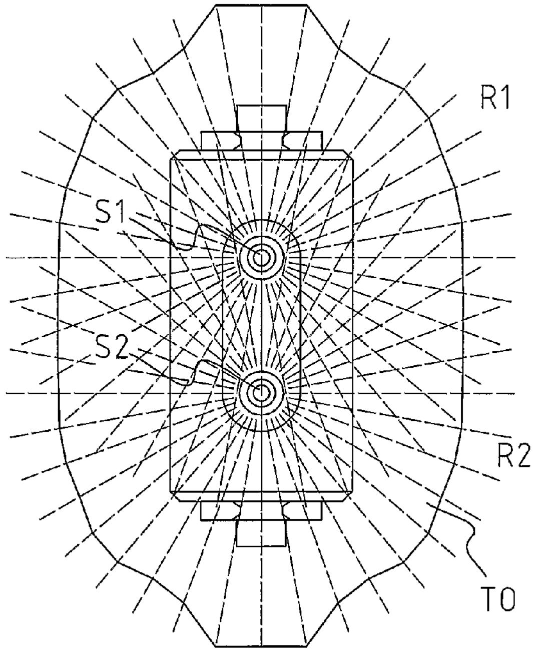
FIG. 5 is a schematic representation of possible radiation patterns from a capsule of radioactive material and a theoretically optimum distribution of radiopaque material for uniform shielding.

The container 1 may be configured and dimensioned such that radioactive material held therein is surrounded by a substantially constant amount of radiopaque material, thus providing a substantially uniform level of shielding in virtually all directions. In order to determine the configuration of the body 2 and lid 3 and to determine the desired wall thickness, estimates of possible radiation patterns may be established. For example, and referring to FIG. 5, since the capsule 16 is shaped such that it cannot be considered a point source of radiation, it has been modelled as having twin point sources S1, S2, at opposite ends of the capsule 16. Radiation patterns R1, R2 for these twin sources S1, S2 were established and superimposed resulting in combined radiation patterns, which yielded a theoretical optimum shape TO of the container. Other theoretical optimum shapes may be appropriate for radioactive materials of other shapes, sizes, and/or number of point sources.

In order to design the body 2 and lid 3 of the container 1 shown in FIG. 1 such that they at least generally exhibit the theoretical optimum shape TO determined for the capsule 16: i) the thickness of the body 2 between the bottom 9 of the recess 4 and its bottom surface 37 and the thickness of the lid 3 between the bottom 10 of its recess 5 and its top surface 38 may both be approximately equal to the thickness of the cylinder wall 14; and ii) the peripheral edge portions 39, 40 of the body 2 and lid 3 may be chamfered.

In order to protect the body 2 and lid 3 against damage during transport and handling, one or both may be disposed in a case 41 made of an appropriate protective material (e.g., a synthetic material). Other embodiments of the body and/or lid may be coated or include a layer of molded protective material that may facilitate guarding against damage. The case 41 includes of a receptacle 42 designed to accommodate at least a portion of the body 2, and a cap 43 designed to accommodate at least a portion of the lid 3. One or both the receptacle 42 and the cap 43 of the case 41 may include a feature to enable the body 2 and/or the lid 3 of the container 1 to be releasably connected therewith. For instance, in the illustrated embodiment, the receptacle 42 and the cap 43 include a plurality of angularly spaced ribs 44, 45 to assist in holding the body 2 and lid 3 (respectively) in a press-fitting. The receptacle 42 and cap 43 can be designed to interconnect with one another in any appropriate manner (e.g., bayonet-type fitting, press-fitting, snap-fitting, and the like). For instance, the illustrated receptacle 42 and cap 43 have threaded edges 46, 47 for screwing these parts together. Further, the case 41 may be designed to provide a seal between the receptacle 42 and the cap 43 when interconnected. For instance, in the embodiment illustrated in FIG. 2, an O-ring 48 is disposed in a groove 49 in the cap 43 of the case 41 for providing a seal between the receptacle 42 and the cap 43.

In an exemplary procedure for using the container 1, the capsule 16 may be disposed in the base 18 of the vial 17 so that the filter layers 28, 29 of the vial 17 are at least generally interposed between the capsule 16 and the base 18. The cap 19 of the vial 17 may then be attached to (e.g., snap-fitted or screwed on) the base 18 to enclose the capsule 16 in the vial 17. The vial 17 may then be placed into the recess 4 in the body 2 of the container 1, and the lid 3 of the container 1 may disposed on the body 2 so that the vial 17 is enclosed therein and so that the closure surfaces 12, 13 face each other and are in close proximity with one another. When placing the lid 3 on the body 2, the protrusion 36 on the vial cap 19 snaps into the insert 32. The body 2 and lid 3, being in a closed condition, may then be placed in the case 41 (e.g., for transport to a healthcare facility).

At the healthcare facility, the radioactive material in the container 1 may be administered to a patient. To this end, the cap 43 of the case 41 may be unscrewed and removed from the receptacle 42. Since the radiation-shielding lid 3 is attached (e.g., via a press-fitting) to the cap 43 of the case 41, and since the cap 19 of the vial 17 is attached to the lid 3 (e.g., via the snap-fitting with the insert 32), this removal of the cap 43 may allow immediate access to the capsule 16 without the need for removing the lid 3 and cap 19 in separate removal steps. Moreover, since the radiation-shielding body 2 is attached (e.g., via a press-fitting) to the receptacle 42 of the case 41, and since the base 18 of the vial 17 is attached to the body 2 (e.g., via the snap-fitting with the insert 31), the receptacle 42, body 2, and base 18 may effectively act as a single unit during the above-described removal.

Figure 8:
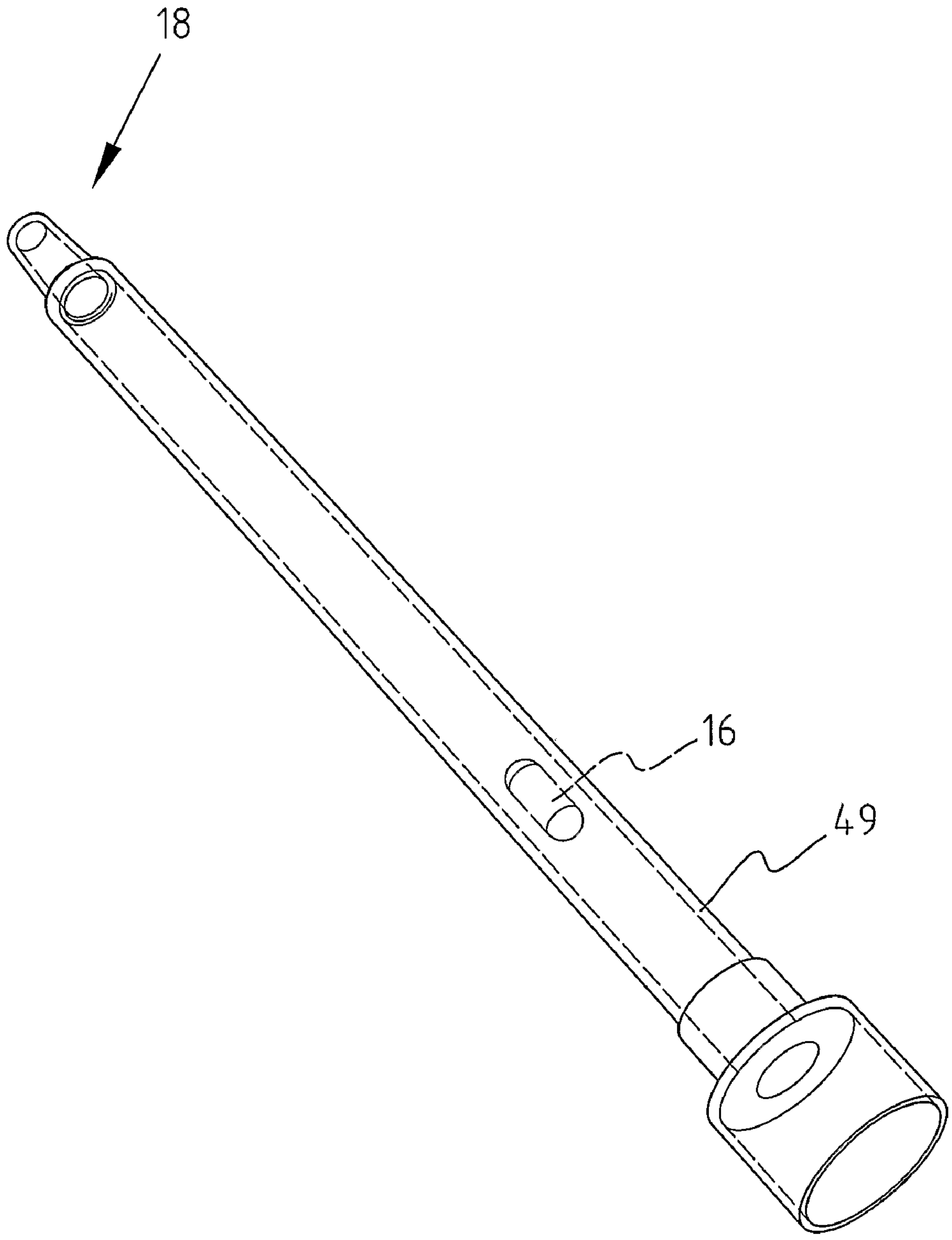
FIG. 8 is a perspective view of the vial and attached administration device during administering of the radioactive material.

An administration device, such as the substantially tubular device 49 shown in FIG. 8, may be utilized to at least assist in administering the capsule 16 to a patient. This device 49 can be releasably connected to the base 18 of the vial 17 in any of a number of appropriate manners. For instance, in the illustrated embodiment, the administration device 49 has a threaded free end 50 designed to threadingly engage a threaded peripheral edge 51 of the base 18 when engaged and rotated. In order to inhibit the base 18 from rotating in the recess 4 when the administration device 49 is screwed thereon, one or both the body 2 and the base 18 may include an anti-rotation locking feature. For instance, in the illustrated embodiment, the locking feature is provided via a combination of the lugs 11 on the edge 15 of the recess 4 and corresponding recesses 52 in the edge 51 of the base 18.

Figure 6:
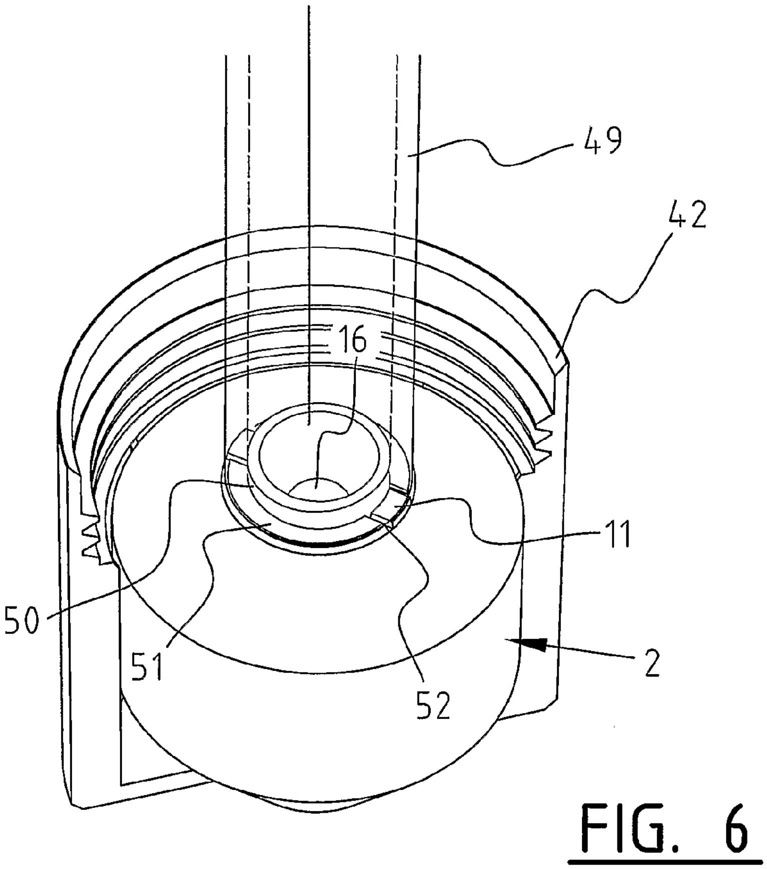
FIG. 6 is a partly broken away perspective view of the container and receptacle bodies with an administration device being connected to the vial.
Figure 7:
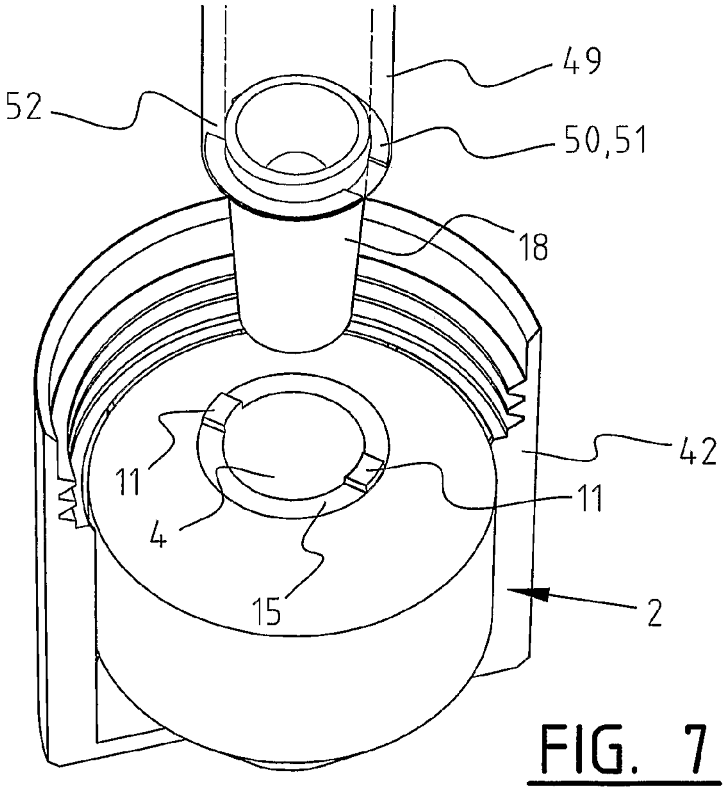
FIG. 7 is a view corresponding to FIG. 6 in which the vial is removed from the container.

After the threaded free end 50 of the device 49 is releasably connected with the base 18 (e.g., screwed onto the base 18 as shown in FIG. 6), the base 18 may be removed from the recess 4 (e.g., by providing a lifting force to the device 49 FIG. 7), and the radioactive material may be administered to the patient. To this end the patient may put an end of the device 49 that opposes the threaded free end 50 to his/her mouth and tip it (FIG. 8), so that the capsule 16 will travel (e.g., slide) through the device 49 into his/her mouth. After the capsule 16 and base 18 of the vial 17 are removed from the container 1 for administration of the capsule 16, the container 1 may be closed, and the device 49 with the base 18 attached thereto may be discarded as radioactive waste.

Figure 9:
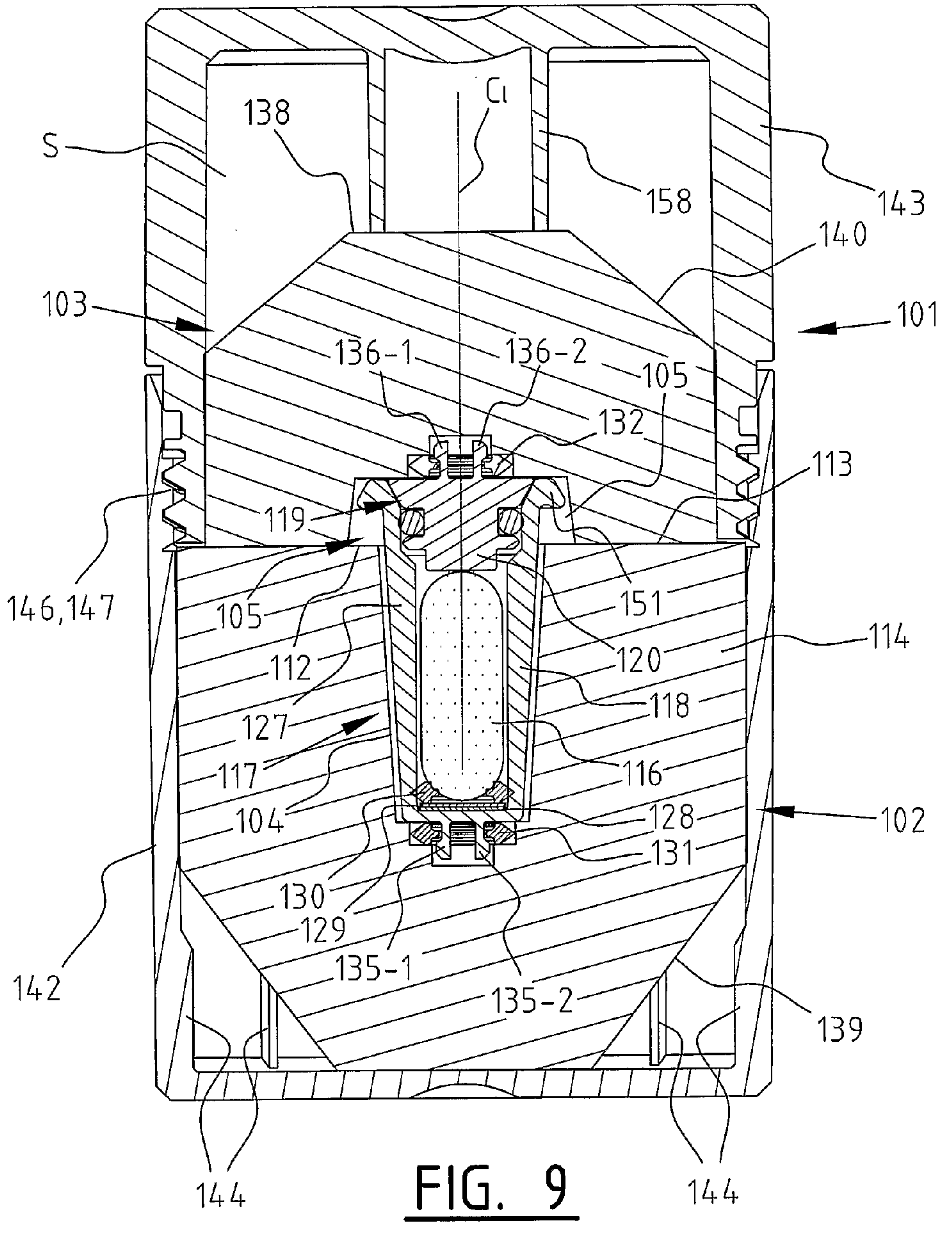
FIG. 9 is a cross-section of another embodiment of a radiation-shielding container of the invention.

FIG. 9 illustrates another embodiment of a radiation-shielding container 101. The closure surfaces 112, 113 of the body 102 and lid 103 (respectively) of this container 101 are substantially perpendicular to the centre line $C_L$. In order to promote the closure surfaces 112, 113 being misaligned with the radiation that is emitted by the radioactive material in the illustrated embodiment, the base 118 and cap 119 of the vial 117 are sized and arranged such that the bottom of the cap 119, which may abut the capsule 116, is below the closure surfaces 112, 113. In other words, an imaginary plane that includes the closure surface 112 does not intersect with any portion of the capsule 116 that is disposed in the recess 104 of the body 102. It is generally preferred that the capsule 116 be substantially immobilized in the vial 117. For instance, in the illustrated embodiment, the capsule 116 is interposed between the cap 119 and the locking ring 130 to promote this substantial immobilization. The locking ring 130 exhibits an arrowhead-like cross-section that may promote locking of the underlying filter layers 128, 129 at the bottom of the base 118.

Still referring to FIG. 9, the cap 119 of the vial 117 is of a somewhat different design than the cap 19 of the vial 17 (FIG. 1). In particular, the cap 119 does not protrude beyond the peripheral edge 151 of the base 118 (e.g., in order to reduce an overall height of the vial 117). Instead, the entire vial cap 119 may be characterized as a plug-like part 120, which is completely inserted into the vial base 118.

The base 118 of the vial 117 differs from the base 18 of the vial 17 (FIG. 1). In particular, the base 118 is relatively long and protrudes (e.g., extends out) from the recess 104 (FIG. 10), such that its peripheral edge 151 is spaced from the closure surface 112 of the body 102 of the container 101. This peripheral edge 151 of the base 118 of the vial 117 serves as a connecting feature that cooperates with a corresponding connecting feature at the free end 150 of another administration device 149. The connecting feature of the device 149 refers to a plurality of angularly spaced resiliently flexible fingers 152, which snap-fit around the peripheral edge 151 of the vial base 118 when the device 149 is pressed onto the vial 117.

Figure 10:
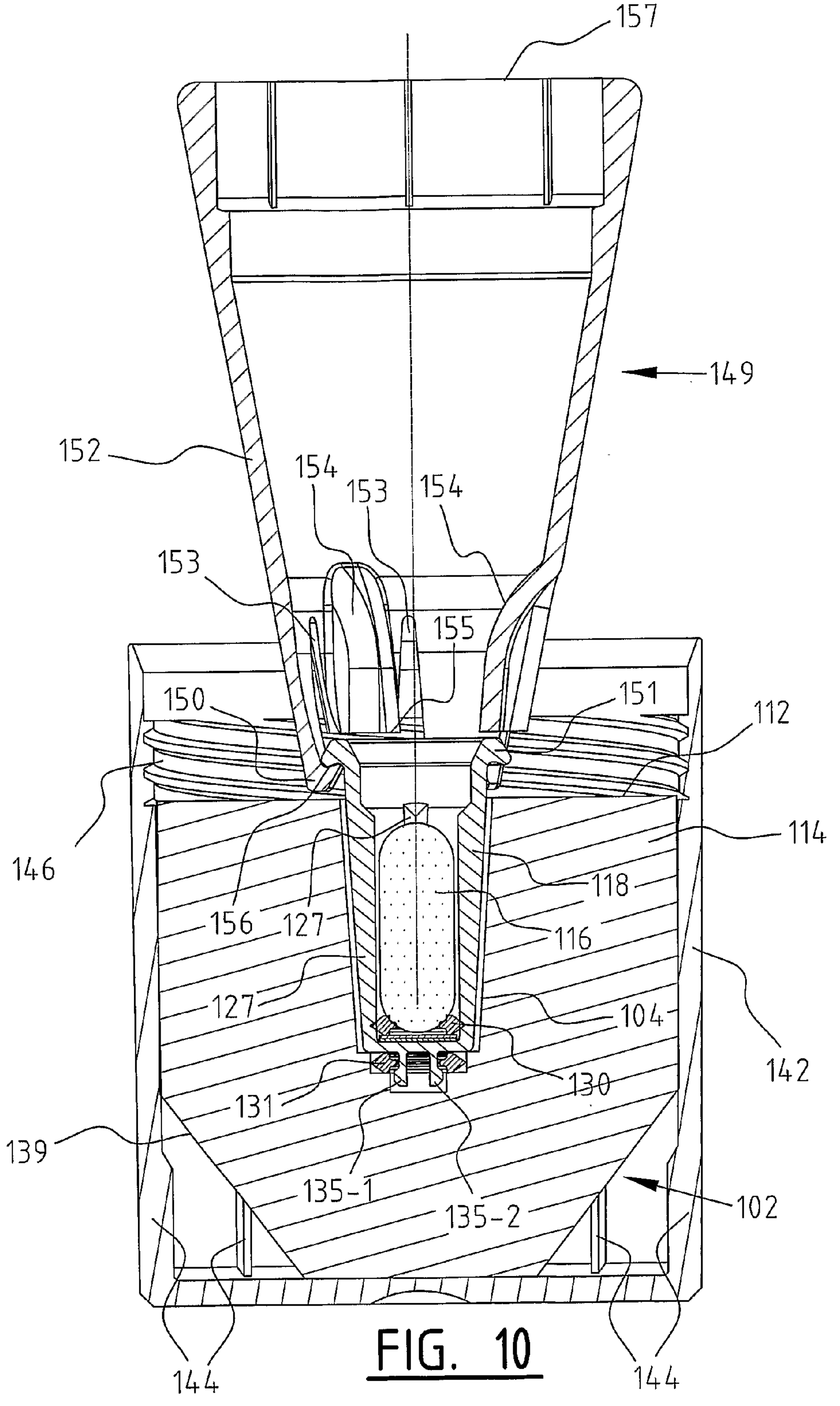
FIG. 10 shows the body of the container of FIG. 9 when an administration tool is connected to a vial.
Figure 11:
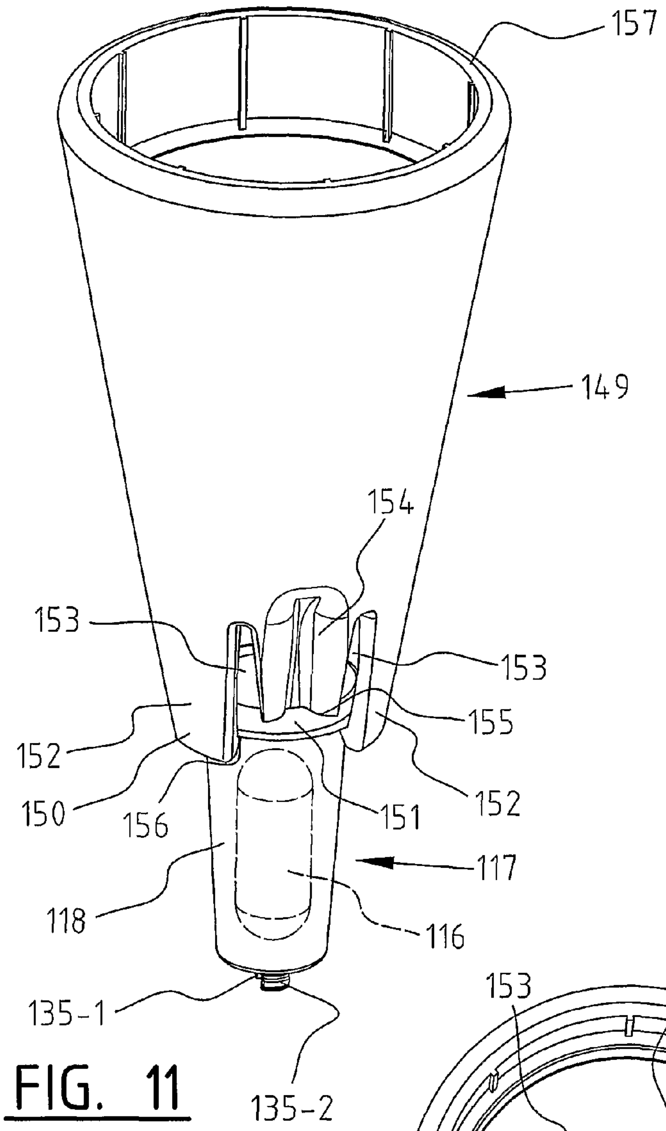
FIG. 11 is a perspective side view of the vial connected to the administration tool.
Figure 12:
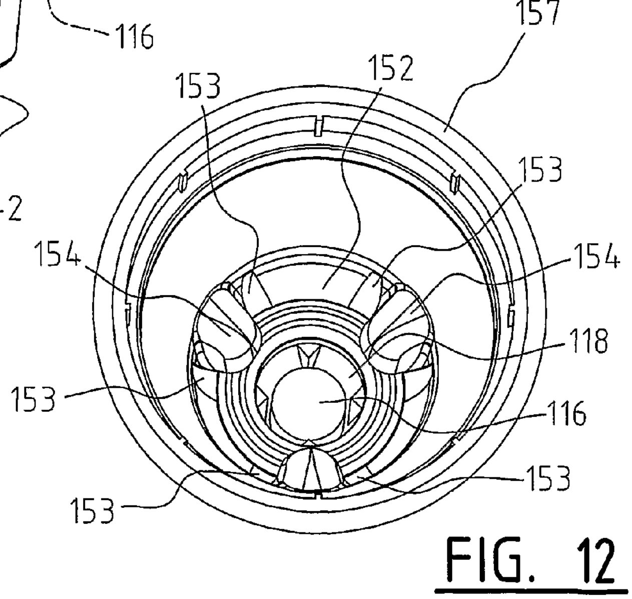
FIG. 12 is a perspective top view of the vial and the administration tool.

Referring to FIGS. 10-11, the device 149 is tapered and substantially tubular. In particular, the device 149 generally exhibits a larger opening diameter toward its upper end 157 than toward its free end 150. In some characterizations, the device 149 may be said to resemble a cup having an open bottom. This design may ease handling of the device 149 and/or facilitate administration of the radioactive capsule 116. The resiliently flexible fingers 152 are bounded on both sides by incisions 153, which are shaped and sized to provide the desired flexibility while inhibiting the radioactive capsule 116 from falling through these incisions 153. Between each pair of fingers 152 is an inwardly extending support part 154.

The distance between lower edges 155 of these support parts 154 and upper edges 156 of the fingers 152 substantially corresponding with the thickness of the peripheral edge 151 of the vial base 118. Some may say that this configuration promotes the vial base 118 being positively and/or securely held between the fingers 152 and the support parts 154.

In order to balance the various forces acting on the vial 117 and to prevent the inserts 131, 132 from being dissociated from the container bottom 102 and/or lid 103 (respectively), the base 118 and the cap 119 of the vial 117 may be include split snapping legs 135-1,135-2 and 136-1, 136-2 (respectively) rather than the solid protrusions 35, 36 of the vial 17 (FIGS. 2 and 4).

The case 141 in which the container 101 is arranged may not include any ribs between its inner walls and the body 102. Some ribs 144 may exist, such as those confined to the part of the receptacle 142 accommodating the chamfered edge 139 of the container body 102. Therefore, one or both the body 102 and the lid 103 of the container 101 may extend all the way to the inner walls of the receptacle 142 and/or cap 143 (respectively). The wall thickness of the receptacle 142 may be reduced in comparison to that of the receptacle 42 of FIGS. 2-3. This reduction in thickness may serve to enhance the case's interior holding capacity.

Referring to FIG. 9, the cap 143 of the case 141 tends to be longer (e.g., measured along the centre line $C_L$) than the cap 43 of the case 41 (FIG. 1). In addition, the cap 143 includes a spacer 158 that may abut the top surface 138 of the lid 103 so as to create a space S above the lid 103. Since the container 101 may be handled by holding the cap 143, this space S may tend to increase the distance between the radioactive material in the capsule 116 and fingers of a person handling the container 101. This may be of importance to some, since the dose rate to which the person handling the container 101 is exposed tends to decease with the square of the distance to the source of radiation.

To administer the radioactive capsule 116 to a patient, the cap 143 of the case 141 may be removed (e.g., unscrewed) from the receptacle 142 of the case 141. Since the radiation-shielding lid 103 is attached (e.g., via press-fitting) to the cap 143 of the case 141, and since the cap 119 of the vial 117 is attached to the lid 103 (e.g., via the snap-fitting with the insert 32), this removal of the cap 143 may allow immediate access to the capsule 116 without the need for removing the lid 103 and cap 119 in separate removal steps. Moreover, since the radiation-shielding body 102 is attached (e.g., via a press-fitting) to the receptacle 142 of the case 141, and since the base 118 of the vial 117 is attached to the body 102 (e.g., via the snap-fitting with the insert 131), the receptacle 142, body 102, and base 118 may effectively act as a single unit during the above-described removal.

The administration device 149 may then be connected to the base 118 of the vial 117 by simply pressing its free end 150 against the peripheral edge 151 until the fingers 152 bend outward and snap around the edge 151. The patient may now lift the body 102 of the container (with the base 118 of the vial 117 disposed therein), put the upper edge 157 of the device 149 to his/her lips, and tip the body 102 so that the capsule 116 travels (e.g., slides) from the base 118, through the device 149, into the patient's mouth.

After the capsule 116 has been administered to the patient, the base 118 of the vial 117 may be removed (e.g., pulled) from the recess 104 using the device 149, after which the base 118 and the device 149 may be discarded as radioactive waste. The lid 103 may be put back onto the body 102 by screwing the cap 143 onto the receptacle 142, after which the container 101 may be stored and/or returned for reuse.

Instead of lifting and tipping the entire body 102, which may be fairly heavy to some users, the patient may choose to use the administration device 149 to remove the base 118 of the vial 117 from the body 102 of the container 101 while the capsule 116 is still disposed in the base 118. Holding the combination of the base 118 and the device 149, the patient may then put the upper edge 157 of the device 149 to his/her lips, and tip the combination so that the capsule 116 travels (e.g., slides) from the base 118, through the device 149, into the patient's mouth. After the capsule 116 has been administered to the patient, the base 118 and the device 149 may be discarded as radioactive waste. The lid 103 may be put back onto the body 102 by screwing the cap 143 onto the receptacle 142, after which the container 101 may be stored and/or returned for reuse.

Figure 13:
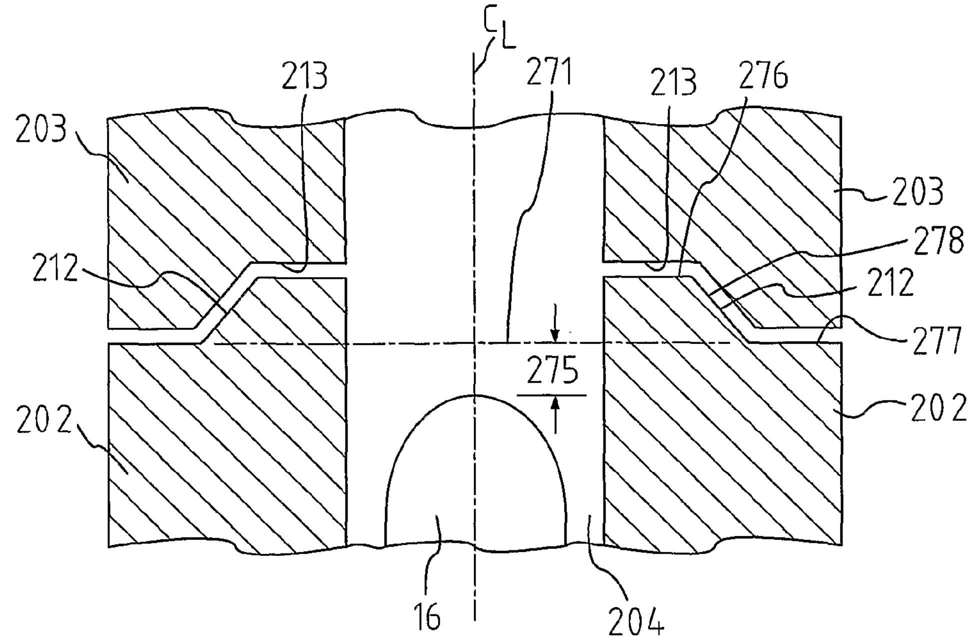
FIG. 13 is a cross-section of another embodiment of a body and lid of a radiation-shielding container of the invention.

FIG. 13 illustrates another embodiment of a radiation-shielding body and lid of the invention. In particular, FIG. 13 illustrates a body 202 and a lid 203, each of which includes radiopaque material (e.g. lead, tungsten, depleted uranium, and/or the like). While they may exhibit any of a number of appropriate designs and shapes, both the body 202 and the lid 203 illustrated in FIG. 13 are substantially rotationally symmetrical about the centre line $C_L$. The body 202 has a recess 204 defined therein for accommodating radioactive material (here, the capsule 16). The body 202 and lid 203 may be joined so that respective closure surfaces 212, 213 thereof are in very close proximity with one another and are preferably in contact. The closure surface 212 associated with the body 202 includes, two-dimensionally speaking, a first substantially flat portion 276, a second substantially flat portion 277, and an angled (e.g., frustoconical) portion 278 located at least generally between the first and second substantially flat portions 276, 277. All of these portions 276, 277, 278 are misaligned with (i.e., not parallel to) the centre line $C_L$. Further, the first and second substantially flat portions 276, 277 are shown as being substantially perpendicular to the centre line $C_L$. Still further, as the angled portion 278 of the closure surface 212 extends radially outwardly, this angled portion 278 tends to exhibit a downward slope (e.g., at least generally toward a bottom surface of the body 202). In a three-dimensional characterization, the portions 276, 277, 278 of the closure surface 212 may be said to be disposed annularly about the centre line $C_L$.

Still referring to FIG. 13, the closure surfaces 212, 213 are substantially complimentary and configured such that at least a portion of each of the closure surfaces 212, 213 is misaligned with radiation directly emanating from the capsule 16. This misalignment of the radiation relative to portions of the closure surfaces 212, 213 is due in part to the design of the closure surfaces 212, 213 and in part to the positioning of the capsule 16 relative to an imaginary reference plane 271 indicative of a plane that is substantially perpendicular to the centre line $C_L$ and including at least a portion of the closure surface 212 (in particular, the second substantially flat portion 277) of the closure surface 212. In particular, the capsule 16 is positioned in the recess 204 so that it is spaced from the reference plane 271 by a distance 275. This distance 275 is of a magnitude such that any radiation directly emanating from the capsule 16 is directed toward the side walls of the body at locations below the reference plane 271 and/or exhibits a radiation vector oriented too closely in line with the centre line $C_L$ to enter a gap (if any) between the closure surfaces 212, 213. As such, even if a small gap exists between the closure surfaces 212, 213 (e.g., because of a manufacturing tolerance and/or damage) when the container 1 is closed, the design of the closure surfaces 212, 213 combined with the positioning of the capsule 16 (relative to the reference plane 271) in the recess 204 tends to prevent radiation leakage. Incidentally, it should be noted that the gap illustrated between the closure surfaces 212, 213 shown in FIG. 13 may not (and preferably does not) actually exist. While not shown, the capsule 16 may be in a vial that is located in the recess 204 in some embodiments. Further, while the body 202 is not shown as including any type of mechanism to hinder rotational movement of a vial disposed in the recess 204, some embodiments of the body 202 may be equipped with an appropriate vial anti-rotation mechanism (e.g., one or more lugs 11). Still further, the body 202 and/or lid 203 may be designed to be disposed in a case such as those described with regard to FIGS. 2 and 9.

Figure 14:
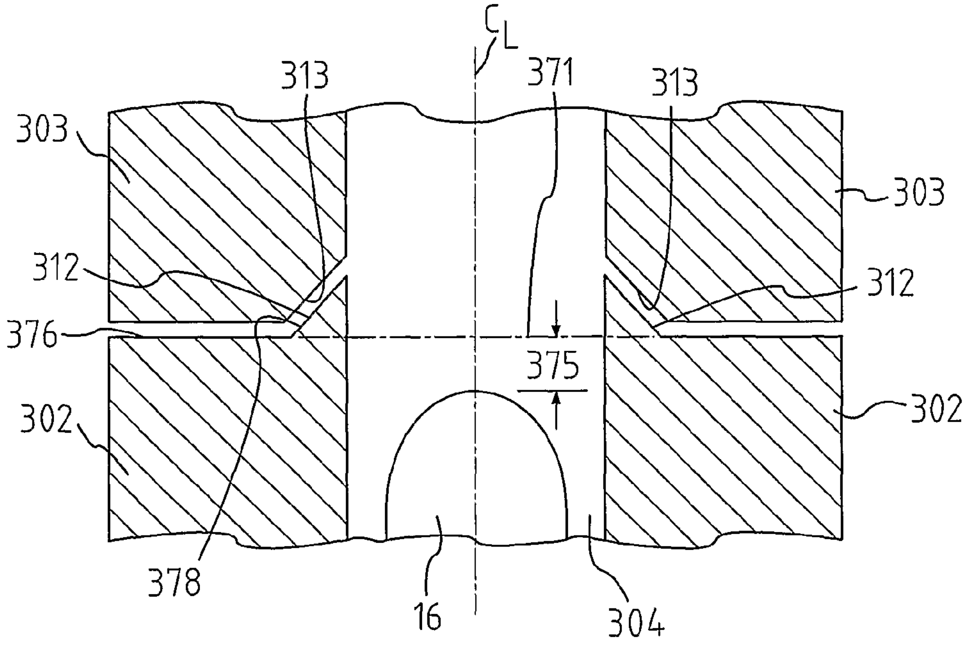
FIG. 14 is a cross-section of still another embodiment of a body and lid of a radiation-shielding container of the invention.

FIG. 14 illustrates yet another embodiment of a radiation-shielding body and lid of the invention. In particular, FIG. 14 illustrates a body 302 and a lid 303, each of which includes radiopaque material (e.g. lead, tungsten, depleted uranium, and/or the like). While they may exhibit any of a number of appropriate designs and shapes, both the body 302 and the lid 303 illustrated in FIG. 14 are substantially rotationally symmetrical about the centre line $C_L$. The body 302 has a recess 304 defined therein for accommodating the capsule 16. The body 302 and lid 303 may be joined so that respective closure surfaces 312, 313 thereof are in very close proximity with one another and are preferably in contact. The closure surface 312 associated with the body 302 includes, two-dimensionally speaking, a substantially flat portion 376 and an angled (e.g., frustoconical) portion 378 located at least generally between the substantially flat portion 376 and the centre line $C_L$. Both of these portions 376, 378 are misaligned with (i.e., non-parallel to) the centre line $C_L$. Further, the substantially flat portion 376 is shown as being substantially perpendicular to the centre line $C_L$. Still further, as the angled portion 378 of the closure surface 312 extends radially outwardly, this angled portion 378 tends to exhibit a downward slope (e.g., at least generally toward a bottom surface of the body 302). In a three-dimensional characterization, the portions 376, 378 of the closure surface 312 are disposed annularly about the centre line $C_L$.

Still referring to FIG. 14, the closure surfaces 312, 313 are substantially complimentary and configured such that at least a portion of each of the closure surfaces 312, 313 is misaligned with radiation that is being directly emitted from the capsule 16. This misalignment of the radiation relative to portions of the closure surfaces 312, 313 is due in part to the design of the closure surfaces 312, 313 and in part to the positioning of the capsule 16 relative to an imaginary reference plane 371 indicative of a plane that is substantially perpendicular to the centre line $C_L$ and including at least a portion of the closure surface 312 (in particular, the substantially flat portion 376) of the closure surface 212. In particular, the capsule 16 is positioned in the recess 304 so that it is spaced from the reference plane 371 by a distance 375. This distance 375 is of a magnitude such that any radiation directly emanating from the capsule 16 is directed toward the side walls of the body 302 at locations below the reference plane 371 and/or exhibits a radiation vector oriented too closely in line with the centre line $C_L$ to enter a gap (if any) between the closure surfaces 312, 313. As such, even if a small gap exists between the closure surfaces 312, 313 (e.g., because of a manufacturing tolerance and/or damage) when the container 1 is closed, the design of the closure surfaces 312, 313 combined with the positioning of the capsule 16 (relative to the reference plane 371) in the recess 304 tends to prevent radiation leakage. It should be noted that the gap illustrated between the closure surfaces 312, 313 shown in FIG. 14 may not (and preferably does not) actually exist. While not shown, the capsule 16 may be in a vial that is located in the recess 304 in some embodiments. Further, while the body 302 is not shown as including any type of mechanism to hinder rotational movement of a vial disposed in the recess 304, some embodiments of the body 302 may be equipped with an appropriate vial anti-rotation mechanism (e.g., one or more lugs 11). Still further, the body 302 and/or lid 303 may be designed to be disposed in a case such as those described with regard to FIGS. 2 and 9.

Figure 15:
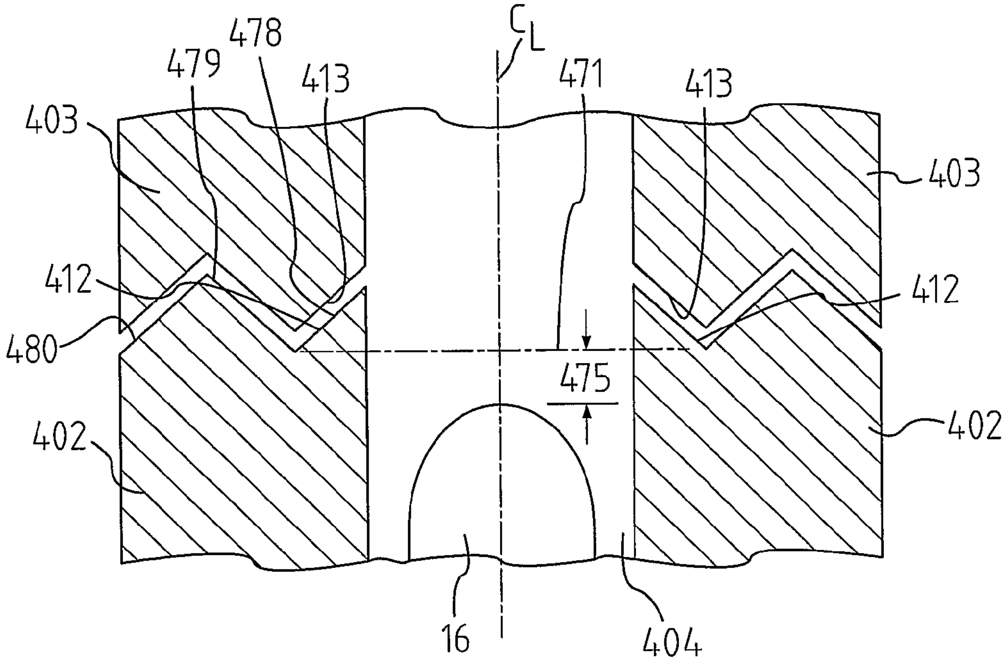
FIG. 15 is a cross-section of yet another embodiment of a body and lid of a radiation-shielding container of the invention.

FIG. 15 illustrates still yet another embodiment of a radiation-shielding body and lid of the invention. In particular, FIG. 15 illustrates a body 402 and a lid 403, each of which includes radiopaque material (e.g. lead, tungsten, depleted uranium, and/or the like). While they may exhibit any of a number of appropriate designs and shapes, both the body 402 and the lid 403 illustrated in FIG. 15 are substantially rotationally symmetrical about the centre line $C_L$. The body 402 has a recess 404 defined therein for accommodating radioactive material (here, the capsule 16). The body 402 and lid 403 may be joined so that respective closure surfaces 412, 413 thereof are in very close proximity with one another and are preferably in contact. The closure surface 412 associated with the body 402 includes, two-dimensionally speaking, a first angled portion 478, a second angled portion 479, and a third angled portion 480. These angled portions 478, 479, 480 in combination make the closure surface 412 exhibit a substantially zigzag configuration. All of these portions 478, 479, 480 are misaligned with (i.e., not parallel to) the centre line $C_L$. Further, none of these portions 478, 479, 480 are substantially perpendicular to the centre line $C_L$. Still further, as the first angled portion 478 of the closure surface 412 extends radially outwardly, this first angled portion 478 tends to exhibit a downward slope (e.g., at least generally toward a bottom surface of the body 402). Conversely, as the second angled portion 479 of the closure surface 412 extends radially outwardly, this second angled portion 479 tends to exhibit an upward slope (e.g., at least generally away from the bottom surface of the body 402). Further, and similar to the first angled portion 278, as the third angled portion 480 of the closure surface 412 extends radially outwardly, this third angled portion 480 tends to exhibit a downward slope (e.g., at least generally toward the bottom surface of the body 402). In a three-dimensional characterization, the portions 478, 479, 480 of the closure surface 412 are disposed annularly about the centre line $C_L$.

Still referring to FIG. 15, the closure surfaces 412, 413 are substantially complimentary and configured such that at least the first angled portion of each of the closure surfaces 412, 413 is misaligned with radiation that is being directly emitted from the capsule 16. This misalignment of the radiation relative to first angled portions of the closure surfaces 412, 413 is due in part to the design of those particular portions of the closure surfaces 412, 413 and in part to the positioning of the capsule 16 relative to an imaginary reference plane 471 indicative of a plane that is substantially perpendicular to the centre line $C_L$ and including at least a portion of the closure surface 412 (in particular, the portion of closure surface 412 nearest a bottom of the body 402). In particular, the capsule 16 is positioned in the recess 404 so that it is spaced from the reference plane 471 by a distance 475. This distance 475 is of a magnitude such that any radiation directly emanating from the capsule 16 is directed toward the side walls of the body at locations below the reference plane 471 and/or exhibits a radiation vector oriented too closely in line with the centre line $C_L$ to enter a gap (if any) between the closure surfaces 412, 413. As such, even if a small gap exists between the closure surfaces 412, 413 (e.g., because of a manufacturing tolerance and/or damage) when the container 1 is closed, the design of the closure surfaces 412, 413 combined with the positioning of the capsule 16 (relative to the reference plane 471) in the recess 404 tends to prevent radiation leakage. Incidentally, it should be noted that the gap illustrated between the closure surfaces 412, 413 shown in FIG. 15 may not (and preferably does not) actually exist. While not shown, the capsule 16 may be in a vial that is located in the recess 404 in some embodiments. Further, while the body 402 is not shown as including any type of mechanism to hinder rotational movement of a vial disposed in the recess 404, some embodiments of the body 402 may be equipped with an appropriate vial anti-rotation mechanism (e.g., one or more lugs 11). Still further, the body 402 and/or lid 403 may be designed to be disposed in a case such as those described with regard to FIGS. 2 and 9.

When introducing elements of various aspects of the present invention or illustrated embodiment(s) thereof, the articles "a", "an", "the" and "said" are intended to mean that there are one or more of the elements. The terms "comprising", "including" and "having" are intended to be inclusive and mean that there may be additional elements other than the listed elements.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as characterized by the following appended claims.

What is claimed is:

1. A radiopharmaceutical assembly, comprising:
- a radiopaque radiation-shielding assembly comprising:
  - a container body comprising a vial receptacle;
  - a container lid configured to couple with the container body;
  - a vial comprising a capsule receptacle and a first fastener component arranged at a base of the vial, wherein the vial is configured to be disposed in the vial receptacle such that the first fastener component releasably couples with a second fastener component arranged at a base of the vial receptacle; and
- an administering device comprising:
  - an elongate hollow tube comprising a central passage having an inner diameter sized to facilitate passage of a radiopharmaceutical capsule therethrough;
  - a vial coupling end configured to releasably couple with the vial to facilitate disengagement of the vial from the vial receptacle, wherein the central passage aligns with the capsule receptacle when the vial coupling end is coupled with the vial; and
  - an oral delivery end, wherein the administering device is configured to facilitate lifting the vial coupled to the vial coupling end above the oral delivery end to facilitate gravitational delivery of the radiopharmaceutical capsule from the vial to the oral delivery end via the central passage.

2. The assembly of claim 1, wherein the radiopaque radiation-shielding assembly comprises lead, tungsten, depleted uranium, or a combination thereof.

3. The assembly of claim 1, wherein the container lid comprises a cap receptacle.

4. The assembly of claim 3, comprising a cap comprising a third fastener component, wherein the cap is configured to cover an opening into the capsule receptacle and wherein the cap is configured to be disposed in the cap receptacle such that the third fastener component releasably couples with a fourth fastener component arranged at a base of the cap receptacle.

5. The assembly of claim 4, wherein the third fastener component comprises a snap-fitting protrusion and the fourth fastener component comprises a snap-fitting receptacle.

6. The assembly of claim 1, wherein the container body comprises a central axis about which the container body is substantially rotationally symmetrical and a body closure surface that extends away from the central axis, wherein at least a portion of the body closure surface is radially oriented at an obtuse or acute angle relative to the central axis.

7. The assembly of claim 6, wherein the container lid comprises the central axis about which the container body is substantially rotationally symmetrical and a lid closure surface that extends away from the central axis, wherein the lid closure surface is radially oriented to correlate with the body closure surface such that the lid closure surface is disposed adjacent the body closure surface in a closed position.

8. The assembly of claim 6, wherein the body closure surface is radially oriented between 30 and 90 degrees relative to the central axis.

9. The assembly of claim 1, wherein the first fastener component comprises a snap-fitting protrusion and the second fastener component comprises a snap-fitting receptacle.

10. The assembly of claim 1, wherein the vial coupling end of the administration device comprises a plurality of flexible fingers arranged to engage a peripheral edge of the vial.

11. The assembly of claim 1, wherein the vial coupling end of the administration device comprises a slot configured to rotatably engage a protrusion on the vial.

12. A radiopharmaceutical administering device comprising:
- an elongated body comprising a first end, a second end, and a central passage extending along the length of the elongated body from the first end to the second end, the central passage comprising an inner diameter sized to facilitate passage of a radiopharmaceutical capsule therethrough;
- a vial lifting feature disposed on the first end and configured to releasably couple with a vial disposed in a shielded container, wherein the vial lifting feature is configured to facilitate disengagement of the vial from a vial receptacle formed in the shielded container and wherein the central passage aligns with a radiopharmaceutical capsule receptacle formed in the vial when the vial lifting feature is coupled with the vial; and
- an oral delivery feature disposed on the second end, wherein the administering device is configured to facilitate lifting the vial coupled to the vial lifting feature above the oral delivery feature to facilitate gravitational delivery of the radiopharmaceutical capsule from the vial to the oral delivery feature via the central passage.

13. The device of claim 12, comprising radiation shielding material.

14. The device of claim 12, wherein the inner diameter narrows from the first end to the second end.

15. The device of claim 12, wherein the vial lifting feature is configured to disengage a snap-fitting between the vial and the shielded container upon coupling the vial lifting feature with the vial and moving the radiopharmaceutical device away from the shielded container.

16. The device of claim 12, wherein the vial lifting feature comprises a plurality of flexible fingers arranged to engage a peripheral edge of the vial.

17. The device of claim 12, wherein the first end comprises a slot configured to rotatably engage a protrusion on the vial.

18. The device of claim 16, comprising gaps between the flexible fingers arranged to prevent the radiopharmaceutical capsule from passing therethrough.

19. A method of using a radiopharmaceutical device, comprising:

coupling a radiopharmaceutical device to a vial disposed in a radiation shielded container;

removing the vial from the container, wherein the removing comprises moving the device away from the container while the device is coupled to the vial; and while the device is coupled to the vial, rotating the device such that the vial is located above an opening defined in the device, wherein the rotating causes a radiopharmaceutical capsule in the vial to move from the vial, through the device, and out the opening in the device.

20. The method of claim 19, comprising uncoupling the vial from the container after the rotating.

21. The method of claim 19, wherein the removing comprises disengaging a snap-fitting between the vial and the container.

22. The method of claim 19, wherein the coupling comprises passing a plurality of flexible fingers extending from the device over a peripheral edge of the vial.

23. The method of claim 19, wherein the coupling comprises rotating the device to engage a slot formed in the device with a projection from the vial.

24. The method of claim 19, comprising disposing the radiopharmaceutical capsule in the vial prior to the coupling.

* * * * *